United States Patent [19]

Oehler et al.

[11] Patent Number: 5,125,514
[45] Date of Patent: Jun. 30, 1992

[54] RECOGNIZING UNWANTED MATERIAL IN TEXTILE FIBERS

[75] Inventors: Oskar Oehler, Zürich; Reinhard Oehler, Berg am Irchel; Robert Demuth, Nuerensdorf; Peter Anderegg, Winterthur, all of Switzerland

[73] Assignee: Maschinenfabrik Rieter AG, Winterthur, Switzerland

[21] Appl. No.: 419,709

[22] Filed: Oct. 11, 1989

[30] Foreign Application Priority Data

Oct. 11, 1988 [CH] Switzerland .................. 03803/88

[51] Int. Cl.⁵ ............................................ B07C 5/34
[52] U.S. Cl. ............................ 209/590; 19/105; 73/160; 73/627; 209/576; 209/644; 367/87
[58] Field of Search ........... 209/590, 576, 552, 906, 209/644, 643; 367/87, 96, 7; 73/159, 160, 624, 628, 633, 627, 629, 599, 865.5; 19/105

[56] References Cited

U.S. PATENT DOCUMENTS

| | | | |
|---|---|---|---|
| 3,485,095 | 12/1969 | Hirata et al. | 73/160 |
| 3,750,461 | 8/1973 | Felix | 73/67.5 |
| 4,095,475 | 6/1978 | Buckley | 73/628 |
| 4,167,803 | 9/1979 | Teichmann | 19/0.2 |
| 4,171,262 | 10/1979 | Lattmann et al. | 209/906 X |
| 4,200,921 | 4/1980 | Buckley | 367/87 |
| 4,481,820 | 11/1984 | Thomann | 73/160 X |
| 4,527,420 | 7/1985 | Foote | 73/627 X |
| 4,542,644 | 9/1985 | Claytor et al. | 73/599 |
| 4,581,935 | 4/1985 | Breazeale | 73/160 X |
| 4,730,493 | 3/1988 | Lebaud et al. | 73/599 |
| 4,819,649 | 4/1989 | Rogers et al. | 73/624 X |
| 4,839,943 | 6/1989 | Leifeld | 19/80 R |

FOREIGN PATENT DOCUMENTS

| | | | |
|---|---|---|---|
| 2902901 | 7/1990 | Fed. Rep. of Germany | 209/590 |
| 792127 | 12/1980 | U.S.S.R. | 209/156 |
| 1141335 | 2/1985 | U.S.S.R. | 73/160 |
| 1193560 | 11/1985 | U.S.S.R. | 73/159 |
| 2095828 | 10/1982 | United Kingdom . | |
| 2202943 | 10/1988 | United Kingdom . | |
| 2210907 | 6/1989 | United Kingdom . | |

Primary Examiner—Donald T. Hajec
Attorney, Agent, or Firm—Burns, Doane, Swecker & Mathis

[57] ABSTRACT

The invention relates to a method of and apparatus for detecting unwanted material in the form of string or woven fabric in a flow of wanted fiber flocks or in a wanted fiber fleece. To this end, the flock flow is guided through a wave field which detects the presence of unwanted material in the flock flow so that the unwanted material can be separated out in a separator facility. The wave field can be an optical or acoustic wave field. The result obtained can, in addition to the separation of the unwanted material, be displayed in display means and/or recorded.

23 Claims, 4 Drawing Sheets

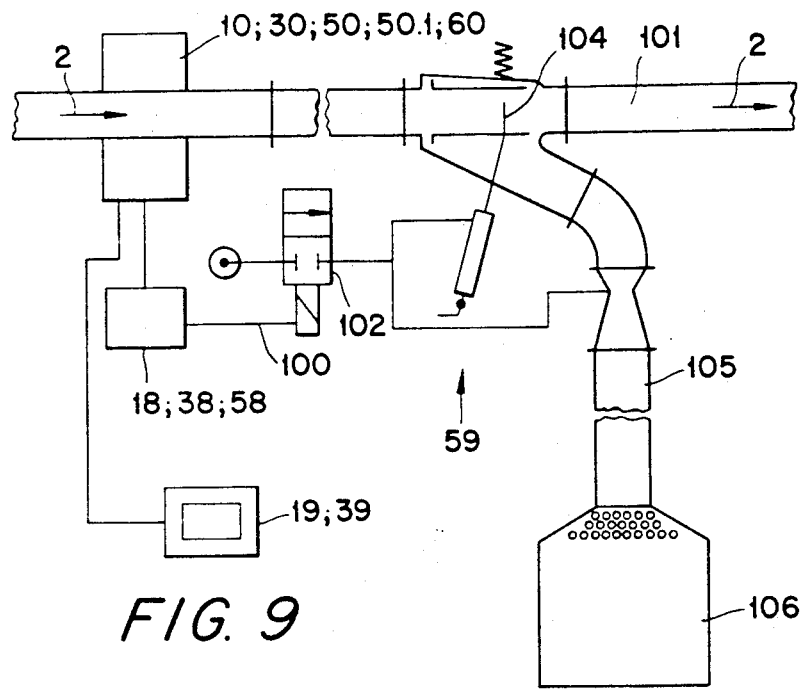
FIG. 9
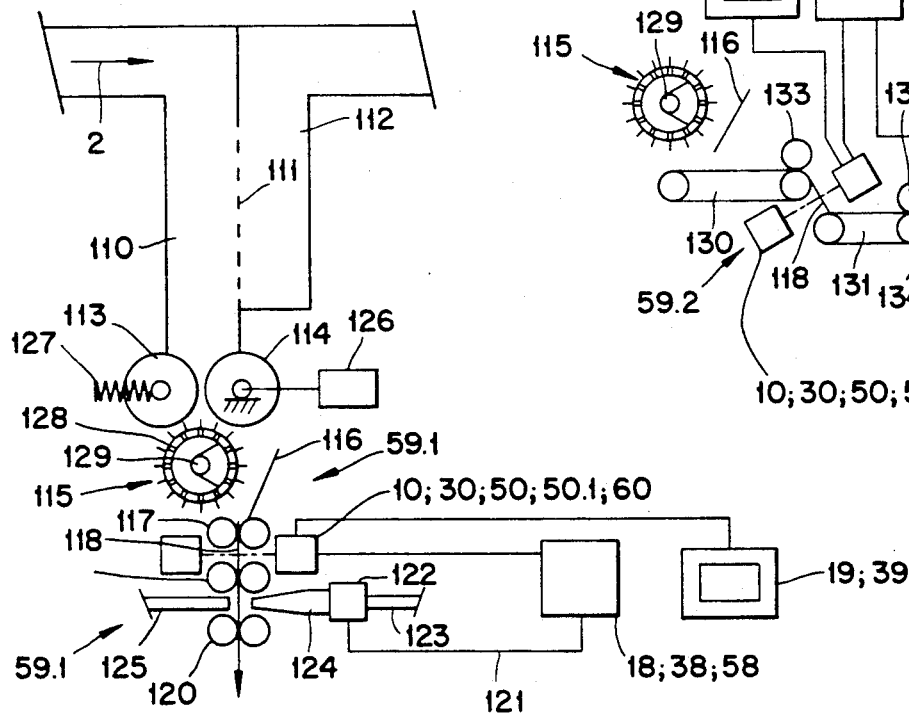
FIG. 10
FIG. 11

RECOGNIZING UNWANTED MATERIAL IN TEXTILE FIBERS

BACKGROUND OF THE INVENTION

The invention relates to an apparatus for and a method of recognizing unwanted material in a flow of fiber material in the textile industry, more particularly spinning plants. The invention further relates to a method and apparatus of recognizing unwanted material in a flow of fiber material in the textile industry, also known as a flow of material under measurement, in the form of an air-fiber mixture conveyed in a pneumatic conveying tube or in the form of a fleece, conveyed so as to be freely or mechanically movable. The invention covers the fields of sensor equipment, acoustics, optics, electronics and data processing. It is concerned with a method of and an apparatus for recognizing unwanted material in the form of string, woven fabrics, strips or foils in a flow of textile raw fiber material.

In the case of textile raw fibers such as raw cotton it is impossible to prevent unwanted material from getting into the raw material. The unwanted material may comprise pieces of metal, pieces of fabric, plastics, foils and tying materials such as strings, bands, threads or the like.

The separation of materials which, in their basic forms, have a structure and quality similar to those of the raw material, such as string material made of jute or synthetic fibers, is uncertain. Unless unwanted material of the latter kind is separated out in time, it goes right through the entire cleaning, carding and fiber-parallelizing processing, is mixed in with the fiber feed materials and is finally spun into yarn together with the wanted material. Because of the reduced tensile strength or poor adhesion between unwanted fibers and wanted fibers, yarn breakages occur during spinning or even as late as the weaving stage. The breakages lead to very undesirable downtimes of the spinning machinery and looms. Further problems occur in the dyeing of yarns or woven fabrics mixed with unwanted fibers since the wanted fibers and unwanted fibers may have different dyeing characteristics. This problem is very serious when the unwanted material is of plastics and the wanted material is a natural product such as cotton.

SUMMARY OF THE INVENTION

There is therefore considerable interest in identifying these difficult to recognize, unwanted substances and separating them out before they reach the carding stage.

Strings or fabrics which pass through a light barrier together with cotton flocks produce very specific signals. The variation in light intensity produced when the flocks of wanted and unwanted material pass the barrier arises because of light scattering. The scattering effect is very considerable since fiber dimensions, which are from 1–50 microns, are of the same order or magnitude as the wavelength of visible light. Consequently, when visible light is used for pattern detection of both wanted and unwanted material, very sharply patterned signals are produced, but these signals have very complicated signal components which are difficult to differentiate from one another.

However, it has been found that when operations are carried out with a kind of radiation whose wavelengths are not of the same order of magnitude as the fiber dimensions (i.e., wanted material) but have a magnitude of the same order as the typical dimensions of the unwanted materials to be identified, results are likely to be better. In the case of strings and fabric yarns these dimensions are typically in the range of from 0.1 to 3 mm.

The production, manipulation and detection of electromagnetic radiation in the latter wavelength range mentioned (i.e., other than visible light) is feasible but tends to be difficult and expensive. This 0.1–3 mm range lies in the area between microwave radiation and infrared radiation.

The use of ultrasonic waves is an alternative to using electromagnetic radiation. Since the speed of sound in air is quite low at 340 m/s, an appropriate field having a wavelength of from 0.1–3 mm can readily be produced, although the temperature dependency of the speed of sound of approximately 0.6 m/s K must be borne in mind.

Ultrasonic signals of the required frequency are usually produced by means of piezoelectric ceramic discs or piezo-foil-like elements. Because of their high acoustic hardness ($h = E\,p$ where E denotes the elasticity module and p denotes the density) as compared with that of air, the matching and, therefore, the energy transmission of the sensor element to air must be considered. As in the method of optical coating, matching can be improved by intermediate layers of appropriate acoustic hardness. When a piezo ceramic is used as a sound generator, quarter-wave plates of plastics are used for sonic impedance matching.

In accordance with the present invention, a method and apparatus are provided for facilitating the recognition and separation of unwanted materials in fiber, strip or fabric form in a flow of wanted fibers.

The present invention relates to a method and apparatus of recognizing unwanted material in a flow of fiber material in the textile industry, also known as a flow of material under measurement, in the form of an air-fiber mixture conveyed in a pneumatic conveying tube or in the form of a fleece, so conveyed as to be freely or mechanically movable, characterized in that, the flow of fiber material interacts with a predetermined wave field produced by a wave generator connected to a signal generator. The wave field, altered because of wave scatter by the interaction between the material being measured and the wave field, is received by wave transducers, and information about the pattern or structure of the material being measured is derived from the electrical signals of the wave receivers.

BRIEF DESCRIPTION OF THE DRAWINGS

Other objects and advantages will become apparent from the following detailed description of preferred embodiments of the invention as described in conjunction with the accompanying drawings wherein like reference numerals are applied to like elements and wherein:

FIGS. 9-11 each show a separating facility for the practice of the method according to the invention.

DETAILED DESCRIPTION OF THE PREFERRED EMBODIMENTS

Figure 1:
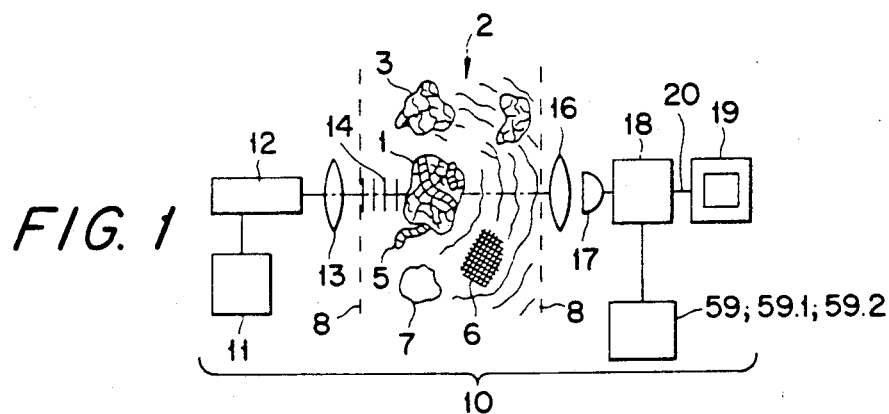
FIG. 1 is a diagrammatic view of a method according to the invention and of an apparatus according to the invention.

FIG. 1 shows an optical apparatus for detecting the light transmission of a flow 2 of material containing a wanted material 3 and unwanted material 5, 6, 7. The wanted material 3 is either fiber material 3 in flock form, such as raw cotton flocks in a conveying tube 8, or a fleece of wanted fibers (as will be later described with respect to FIGS. 10 and 11) in a fleece stack. The unwanted material can be, for example, strings 5, fabrics 6 or foil pieces 7. A visible light beam 14 produced in a source comprising a power supply 11 and a light emitter 12 (e.g., a laser) and directed possibly by means of an optical system 13 on to the material 1 to be measured in the flow 2 is altered by the material 1. The light emitter 12 produces a light having a wavelength on the order of magnitude of the dimensions of the wanted material 3 (e.g., 1-50 microns). The alteration is the result more particularly of the beam being scattered on the fibers and possibly of light absorption in the dyed material 1. Consequently, as the flow 2, also the flow of fiber material, passes through, the light detector 17 receives, possibly by way of an associated optical system 16, a light intensity signal varying in time and converts such signal into an electrical signal. The same is processed, for example, amplified, in a signal processor 18, and smoothed or subjected to signal level discrimination. The signal processor 18 can also comprise a pattern analyzer as will be described with respect to FIG. 7 which is adapted to detect the material 1 and which possibly assesses the same as regards unwanted material 5, 6, 7 present in it. Display means 19, to which the signal processor 18 can be connected, gives a visual display of the received pattern. The display means 19 are of use for making monitoring measurements and can take the form, for example, of a recorder or of a cathode ray tube oscilloscope. To sample the flow 2, either a number of light beams can be disposed one beside another or, for example, the flow 2 can be sampled by means of a rotatable optical system 13 at the emitter 12 and of a corresponding optical system 16 associated with the detector 17.

Figure 2A:
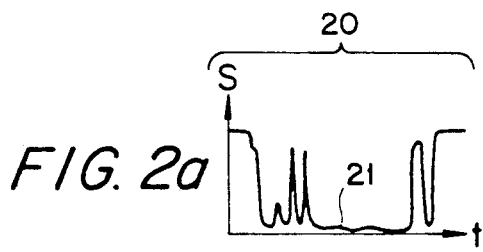
FIGS. 2a, 2b and 2c each show the pattern in time of a detector signal rising from the presence of wanted and/or unwanted material in a fiber material flow shown in FIG. 1.
Figure 2B:
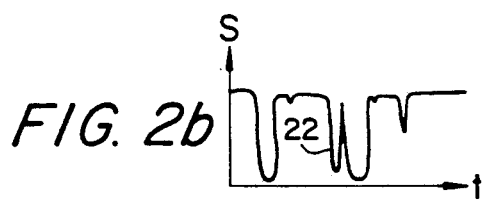
Figure 2C:
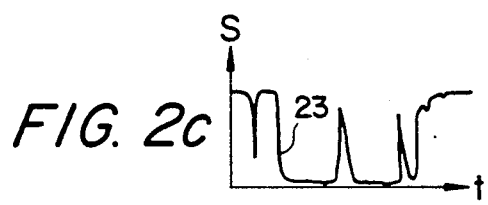

FIGS. 2a, 2b, and 2c show a pattern in time of the light signal received at the detector 17 as various samples 1 pass through the light beam 14 of a laser light source. In this case (i.e., where a laser is the light source) the use of an additional optical system 13, 16 is unnecessary. As FIG. 2a shows, even a very loose cotton flock 3 having a density of 0.03 g/cm³ produces a very substantial attenuation 21 of the laser beam 14, because the discrete cotton fibers, being of a diameter comparable with the wavelength of visible light, produce substantial light scattering. FIG. 2b shows the signal produced at the detector 17 when a string knot 5 passes by. The individual passages of pieces of string also produce a very specific waveform which can be clearly detected thanks to the drop in light transmission. FIG. 2c shows the situation for the passage of a cotton flock mixed with string 5. The string used for FIG. 2b was used in FIG. 2c. As can be seen from FIGS. 2a-c, very sharply patterned signals are produced, but very complicated signal components are present in both the wanted and the unwanted material. Although these signals could therefore be used to distinguish wanted material from unwanted material via, for example, a pattern analysis (as will be described later), because each of the detected signals includes complicated frequency components, such a distinction would be difficult.

Figure 3:
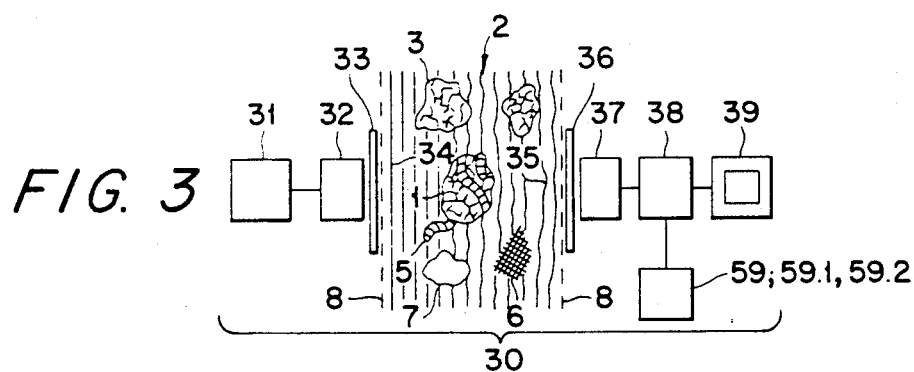
FIG. 3 shows a variant of the method and apparatus according to the invention.

FIG. 3 shows a more preferred embodiment of the present invention having a measuring system 30 in which an ultrasonic field 34 is used as a test beam. This system comprises a signal generator 31, for example, a sinusoidal or rectangular generator, whose output signal is supplied to an ultrasonic transducer operated as an ultrasonic transmitter 32. The emitted sonic field 34, possibly modified by an ultrasonic focusing system 33, impinges on the material 1 and is scattered or absorbed thereby. The disturbed subsonic field 35, possibly after passing through the ultrasonic focusing system 36, is detected by the ultrasonic receiver 37 and the corresponding electrical signal is supplied to a signal processor 38 where the envelope of the high-frequency signal is determined, then supplied to display means 39 for monitoring purposes. The signal processor 38 can comprise image pattern recognition means as will be described with respect to FIG. 7 to recognize the unwanted material 5, 6, 7. Similarly, the signal processor 38 can, if required, respond to the presence of recognized unwanted material by producing a signal causing the flow 2 of material to be deflected.

Figure 4A:
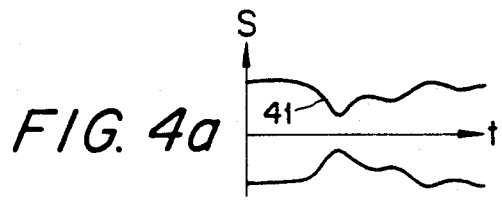
FIGS. 4a, 4b, and 4c each show the pattern in time of a detector signal produced by a flow of pure fiber material and of a flow of fiber material mixed with unwanted material.
Figure 4B:
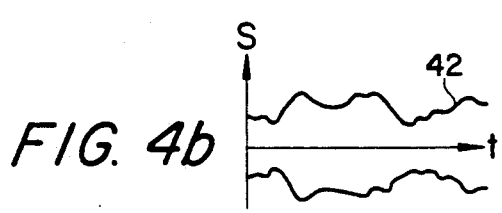
Figure 4C:
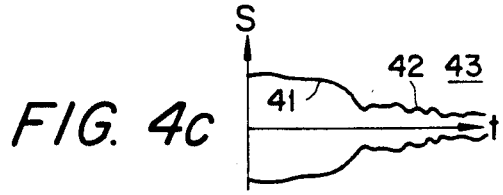

FIGS. 4a, 4b and 4c show typical variations in time of the envelopes of the subsonic signal for interaction of the material 1 with an ultrasonic field 34. FIG. 4a shows the passage of a pure cotton flock, FIG. 4b shows the passage of a string knot and FIG. 4c corresponds to the passage of a cotton flock mixed with string. Since the frequency of the ultrasonic signal is 98 kHz, the wavelength of 3.5 mm corresponds to a string diameter but exceeds the diameter of the cotton fibers by a factor of approximately 100. Consequently, a flat ultrasonic attenuation 41 can be seen in FIG. 4a whereas the string produces a peaky patterning 42 of the envelope in FIG. 4b. In the ultrasonic intensity envelope 43 for the passage of cotton flock mixed with string, the flat pattern 41 of the flock is clearly distinguishable from the peaky pattern 42 of the string 5. Thus, using the FIG. 3 embodiment, a much more desirable distinction between wanted and unwanted materials can be made than was possible in the FIG. 1 embodiment, due to the use of a transmitted signal having a wavelength as described above.

The exact wavelength and frequency of the transmitted signal should, as described above, depend on the dimensions of the wanted and unwanted material. As further described above, a wavelength range of 0.1-3 mm constitutes a usable range for the unwanted material referred to in the exemplary embodiments. For purposes of a preferred embodiment of the present invention, a possible range of wavelengths for the transmitted signal in the exemplary embodiments might therefore correspond to 0.1–10 mm. However, it should be recognized by one skilled in the art, that because cotton fiber dimensions are typically about 10 microns, a most preferred wavelength range for the transmitted signal would be approximately 0.1 to 1 mm, which corresponds to a signal having a frequency of approximately 100 KHz.

Figure 5:
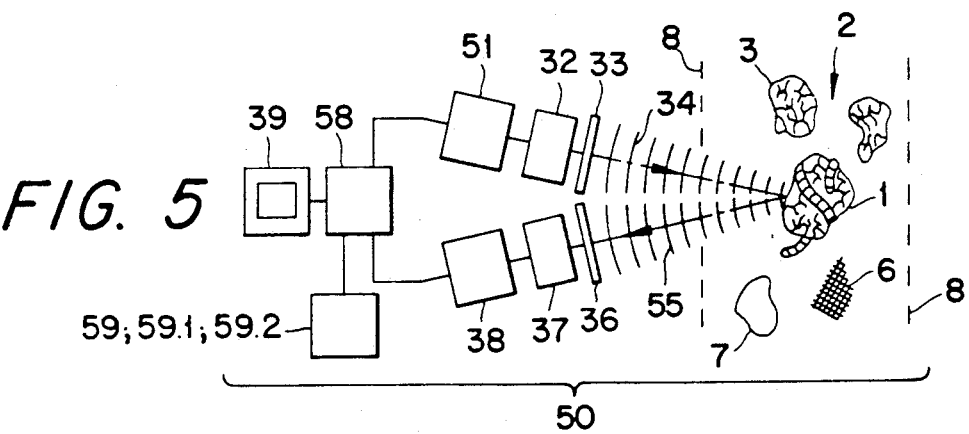
FIG. 5 shows another variant of the apparatus according to the invention, the transmission system being replaced by a reflection system.

FIG. 5 shows another more preferred method of measuring the interaction of an ultrasonic field with the material 1 wherein, as opposed to using the continuous wave source of the previously described embodiments, a pulsed wave source is utilized. An ultrasonic signal 34 contacts the material 1, the latter either being material in flock form passing through a conveying tube or being a fleece. In contrast to the system of FIG. 3, the ultrasonic transmitter 32 produces, by means of the electrical signals of an ultrasonic pulse generator 51, short ultrasonic wave trains instead of signals whose amplitude is constant in time. The wave trains are reflected by the material 1. Echo signals 55 are either received by the transmitter 32 or detected by a second ultrasonic receiver 37 and processed in a signal processor 38. From the time delay between the ultrasonic pulse transmitted by the transmitter 32 and the echo received by the receiver 32 or 37, a correlator 58 can calculate the distance of the sound-reflecting material 1 from the transducers 32, 37. If required, image pattern recognition means present in the correlator 58 can detect the unwanted material 5, 6 or 7 and produce corresponding signals to divert the flow 2. For example, the correlator 58 could use the signal detected by the receiver 32 or 37 to recognize the intensity or magnitude of the reflected echo as will be described more fully with respect to FIG. 8. The reflected pulse must, however, be scaled to account for the distance of the particle from the detector. Accordingly, the correlator 58 uses the time delay between the transmitted signal and the reflected echo to determine this distance and thus properly proportion the reflected echo.

As already shown in, for example, FIGS. 4a, 4b and 4c, the ultrasonic method according to the invention makes it possible to distinguish the loose structure of a cotton flock 3 from the structure of a tightly braided string 5. The question arises of evaluating this information. Pattern recognition methods are inherently suitable for this task. The fast computers that are now available make it readily possible to recognize the presence of acoustically dense unwanted material, such as string 5 and fabric 6, in the loose flock flow 2 or in a fleece. However, since the flow 2 must be continuously monitored laterally as well, either a large number of measuring facilities 32, 37 disposed one beside another are necessary or a test beam must be guided laterally over the flow 2 or, in the case of FIGS. 10 and 11, the fleece 118 (scanning).

The question arises, however, of how to recognize the pattern of unwanted material by simple measurement means. In this connection the spatial frequency analysis of the ultrasonic signal disturbed by the material being measured can help to reduce the data analysis effort considerably. The use of a spatial frequency analysis will now be described in conjunction with a further exemplary apparatus of the present invention which is illustrated in FIG. 6.

Figure 6:
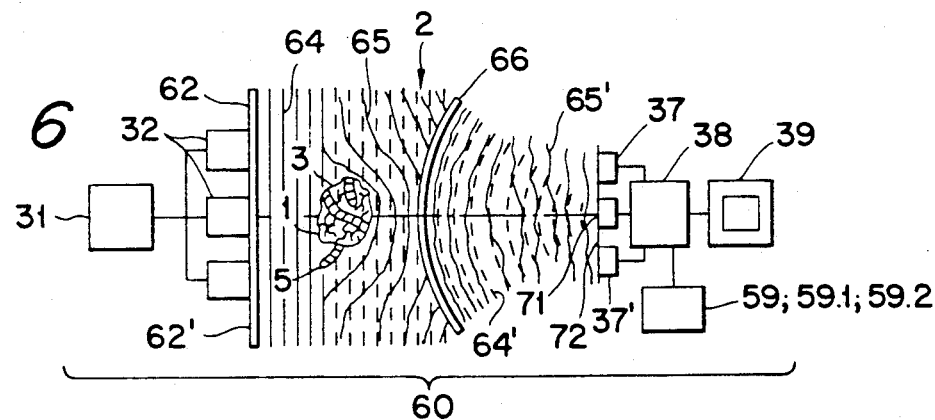
FIG. 6 shows a diagrammatic view of a constructional variant of the system according to the invention.

FIG. 6 shows the construction of a facility 60 for ultrasonic spatial frequency analysis. The facility 60 comprises a signal generator 31, an ultrasonic transmitter 32 producing an extended plane or curved or ultrasonic field 64, an ultrasonic focusing system 66 and the ultrasonic detector 37. The ultrasonic transmitter 62 is embodied either by an arrangement of various discrete transmitters 32, 32' and so on or by a single ultrasonic transmitter 62' of appropriate shape and possibly by a small number of large-area ultrasonic transmitters 62' of appropriate shape. Disposed in the ultrasonic field 64 is a known focusing system 66 which in the absence of material 1 focuses the field 64 on a focal point 71. The known focusing system 66 for the transmitted ultrasonic signal includes, for example, a spherically shaped plate having plural slits for transforming the planar waves into a series of circular shaped waves. The system 66 can be omitted if the extended transmitter 62 has an appropriate focusing curvature. Preferably, and as shown in FIG. 6, the system starts from a plane sonic field 64 which is bunched by the system 66 disposed beyond the flow 2.

The presence in the sonic field of material 1 disturbs the field. It therefore becomes impossible to bunch the field 65' at the focal point 71. An ultrasonic intensity distribution 70 (FIG. 7) is observed in the focal plane 72—i.e., in the plane which contains the focal point 71 and which is parallel to the plane field 64. The distribution 70 provides specific information about the ultrasonic scatter properties of the material being measured. As in the case of an optical system, the distribution 70 represents the Fourier transform due to the scattering object 1 when it is subjected to a plane field 64. The intensity distribution 70 in the focal plane 72 is therefore called the spatial frequency spectrum 70.

Figure 7A:
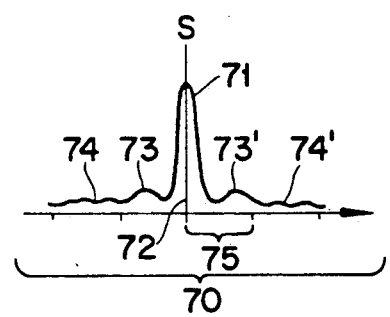
FIGS. 7a and 7b show the pattern of a spatial frequency spectrum of a flow of wanted fiber flocks mixed with unwanted material.
Figure 7B:
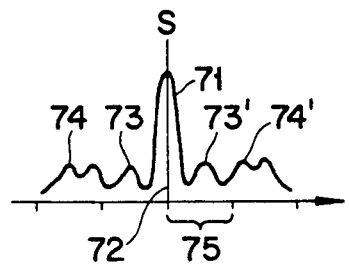

The ultrasonic spatial frequency spectrum 70 will now be described in greater detail with reference to FIGS. 7a and 7b. The central focal point 71 in which the field 64' is focused in the absence of disturbance by the material 1 corresponds to the spatial frequency 0. A sound-scattering object in the plane field 64 leads to a patterned spatial frequency spectrum 70 which has side bands 73, 73', 74, 74', the bands 73, 73' which are adjacent the focal point 71 corresponding to low spatial frequencies and the bands 74, 74' further away from the focal point 71 corresponding to high spatial frequencies. Just as in optics, the low spatial frequencies describe the coarse pattern and the high spatial frequencies relate to sharpness of image. The low spatial frequencies 73, 73' correspond to the flat ultrasonic signals such as may be associated, for example, as shown in FIG. 4a, with a pure cotton flock. The corresponding spatial frequency spectrum 70 is shown in FIG. 7a. The low signal level at the high spatial frequencies 74, 74' is noteworthy.

If the ultrasonic signal has a peaky pattern, as occurs, for example, when a string is present in the ultrasonic field as shown in FIG. 4b, the corresponding spatial frequency spectrum 70 has appreciable signal levels at high spatial frequencies 74, 74'. since, as FIG. 4c shows, even when a cotton flock 2 is mixed with a string 5 the two kinds of ultrasonic patterns can be differentiated, the unwanted material 5, 6, 7 can be reliably recognized on the basis of a partial frequency analysis. FIG. 7b shows the corresponding spatial frequency spectrum 70 in which the signal at the high spatial frequencies 74, 74' respectively is high as compared with the spectrum of the pure cotton flock as shown in FIG. 7a. The problem of pattern recognition is therefore greatly simplified.

Spatial frequency analysis therefore reduced data quantity enormously.

In the system described with reference to FIG. 6 it was assumed that the material 1 is present in an ultrasonic field 64 which is subsequently focused by means of the ultrasonic focusing system 66. As previously mentioned, it is possible in principle to use a focusing transmitter arrangement and to position the material 1 in the divergent ultrasonic field. In this case a spatial frequency spectrum 70 is also produced. However, a scale factor 75 (see, e.g., FIG. 7a) of such a spectrum depends upon the position of the material 1 in this divergent field. For example, parts of the material 1 disposed immediately after the respective focusing system 62, 66 have a higher spatial frequency scale factor 75 than parts near the focal point 71. The roughness of an object 1 may therefore easily be associated with high spatial frequencies 74, 74' or low spatial frequencies 73, 73', depending on the position of the object 1 in the divergent field; even then, however, apparatuses of large dimensions are necessary, which is a disadvantage because of the high air absorption losses of the high-frequency ultra-sound of a wavelength in the 1 to 3 mm range.

As in a plane optical field, the scale factor 75 in a plane ultrasonic field is independent of the position of the material or object 1 in the ultrasonic field 64. Objects 1 near the transmitter and objects 1 disposed directly before the focusing system 66 therefore give rise to the same spatial frequency spectrum 70, an important conclusion for the possibility of evaluating the spatial frequency spectrum of physically elongated articles.

The ultrasonic field 64 interacting with the material or object 1 need not necessarily be plane—i.e., constant in two dimensions. If the material 1 is, for example, movable as a flow 2 or if the ultrasonic transmitter 62 can be guided over the material 1, all that is necessary is for the field 64 to be constant transversely to the flow 2 or to the direction of movement of the ultrasonic transmitter 62 (i.e., a linear field, constant in one dimension). In this case, the field cannot in the absence of material 1 be focused on a focal point 71 but can be focused merely on a line, the focal line 71'. A spatial frequency analysis can be performed by scanning the ultrasonic field 65' along the perpendicular to the focal line 71' in the focal plane 72.

Figure 8:
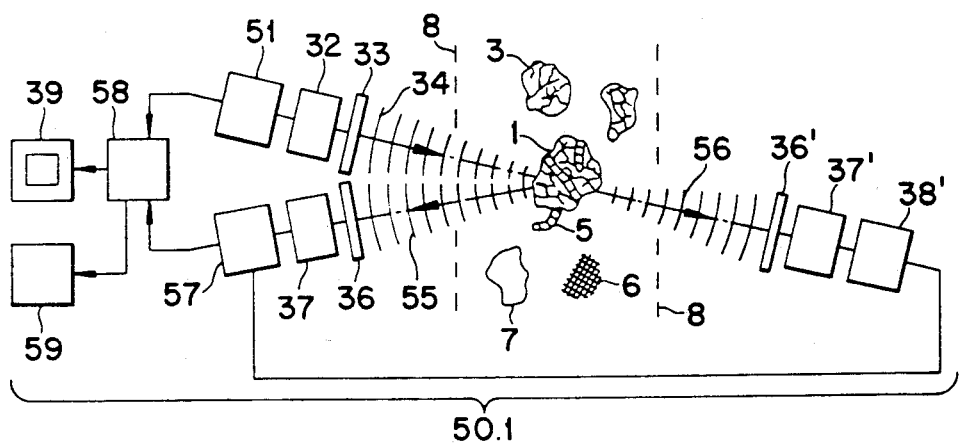
FIG. 8 shows a variant of the method and apparatus of FIG. 5.
Figure 8A:
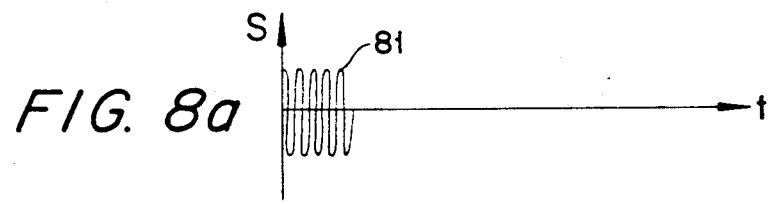
FIGS. 8a, 8b, 8c, 8d and 8e each show a pattern of a spatial frequency spectrum of the signals of the apparatus of FIG. 8.
Figure 8B:
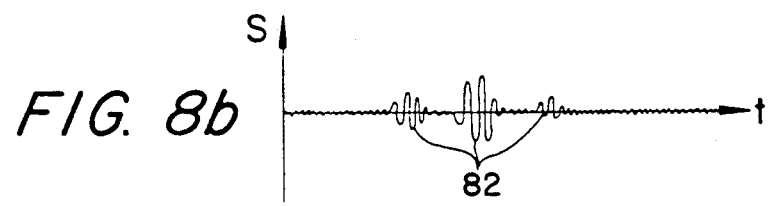
Figure 8C:
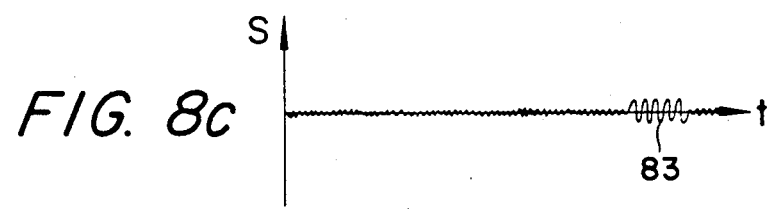
Figure 8D:
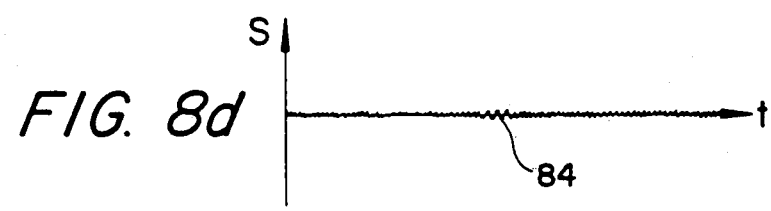
Figure 8E:

The recognition of the pattern in accordance with the FIG. 5 embodiment will now be more fully described with reference to FIG. 8. FIG. 8 represents a further development of the method described with reference to FIG. 5, whereby greater precision can be attained when desired. The method according to FIG. 8 uses an additional ultrasonic receiver 36', 37', 38' to detect an ultrasonic pulse 56 transmitted through the material 1. The timing is shown in FIGS. 8a-8e. If the flow 2 contains no unwanted material 5, 6, 7, no marked ultrasonic echo pulse 84 is formed and the transmitted ultrasonic pulse 81 reaches the receiver unit 36', 37', 38' in a form 85 suffering little attenuation. If the material 2 contains unwanted material 5, 6, 7, ultrasonic echo pulses 82 which depend on the pattern, size and position are formed and are received either by the transmitter device 32, 33 itself or by an ultrasonic receiver facility 36, 37. The unwanted material 5, 6, 7 may attenuate the transmitted ultrasonic pulse 83 received by the receiver unit 36', 37', 38'. The two signals 82, 83—or if there is not unwanted material 5, 6, 7 in the material 2, the signals 84, 85—are processed in the subsequent signal processor 57 and supplied to the correlator 58, which if unwanted material 5, 6, 7 is detected, operates the separator 59.

That is, the signal processor 57 of FIG. 8 controls amplification of the echo pulses 55 in dependence upon the signal strength of the transmitted ultrasonic pulses 56 which are received by the receiver unit 37'. For example, a ratio of the echo pulse and the transmitted pulse can be established by element 57. Thus, relatively weak echo pulses 55 produced by unwanted material 5, 6, 7 can be evaluated reliably without the inclusion, in the case of a flow of pure fiber material, of discrete cotton flocks—i.e., material which is not unwanted material. Again, as with the FIG. 5 embodiment, the detection of the particle's distance from the receiver unit 37 can be determined in order to properly scale the magnitude of the echo pulses since the proximity of the detector to the material being measured will affect the strength of the detected signals. For example, a table could be created of the echo pulse magnitudes which correspond to wanted and/or unwanted material a given distance from the detector.

The use of the reference numbers 36', 37', 38' for the ultrasonic receiver unit indicates that these are the same elements which have been described with reference to FIGS. 3 and 6 and which are used merely in this variant embodiment.

Also, the signal processor 38 or correlator 58 controls not only display means 39 but also, and more importantly, a separator. The Applicant has described a separator of this kind in the European patent specification having the publication No. 0 000 033. The control primarily includes the actual separating elements—i.e., a control valve and a tube junction or switch which is disposed in a pneumatic conveying line, changes over in response to a control signal and diverts the unwanted part into a receptacle.

FIG. 9 shows a separator 59 controlled via a control line 100 by the signal processor 18 or 38 and correlator 58. The signal processor receives the signals of the measuring facility 10, 30, 50, 50.1 or 60.

The separator 59 is known per se from the European patent application 0 000 033 previously mentioned, such that only the main elements will be referred to again here.

The flow 2 of fiber material is supplied by way of a pneumatic conveying tube 101 for a purpose, which need not be specified here, in the blow room of the spinning works.

When the measuring facility detects unwanted material, the signal processor 18, 38, 58 calculates the instant of time at which a valve 102 operates a pneumatic cylinder 103 so that a tube switch or junction 104 will divert the flow 2 into a bypass 105. The separated unwanted material is therefore conveyed to a waste receptacle 106.

It should be noted that the referencing of the elements of the separator in FIG. 9 does not correspond to the referencing in the European patent application previously referred to.

Also, those elements which have already been mentioned earlier are not mentioned here but merely given like reference numbers in FIG. 9.

FIG. 10 shows a variant of a separator facility 59.1.

In FIG. 10 the fiber flow 2 is guided into a separator 110 in which the material 2 accumulates up to a predetermined level and the air can escape through a perforated plate 111 into an air exhaust shaft 112 for extraction by a source of negative pressure.

The material 2 which has accumulated in the separator 110 is supplied by feed rollers 113, 114 to an opening cylinder 115 which continuously opens the material 2 into fine flocks and hurls them on to a baffle plate 116.

From the baffle plate 116 the fibers go between a first squeezing roller pair 117; the same condense the fibers or fine flocks thereof into a fine fiber fleece 118 which because of the tangled state of the fibers, is of adequate strength. The fleece 118 goes to a second squeezing roller pair 119 and then to a third squeezing roller pair 120. The measuring facility 10, 30, 50, 50.1 or 60 measures the fleece 118 between the first roller pair 117 and the second roller pair 118 and the signal is supplied to the processor 18, 38, 58.

By way of control lines 121 the processor 18, 38, 58 controls a predetermined number of pneumatic valves 122 whose inputs are connected to a compressed air line 123 and whose outputs are connected to a nozzle 124. The nozzles 124 extend between the second roller pair 119 and third roller pair 120 and when instructed by the signal processor, blow compressed air into the fleece 118 so that, depending on the number of nozzles 124 distributed over the whole width of the fleece 118, only that part thereof is blown into a suction line 125 in which the corresponding unwanted material detected by the measuring facility is present. Of course, a very large number of nozzles 124, or displaceable nozzles 124, and, therefore, a corresponding number of valves 122, are distributed over the width of the fleece to ensure that the pieces of fleece to be removed are very small.

Also, of course, the signal processor 18, 38, 58 calculates the period of time between detection of the unwanted material and the instant at which it is ejected. The fleece delivered by the final—i.e., third—squeezing roller pair 120 can go, for example, to a feed chute of a card. If required this fleece can be opened again into flocks by an opening cylinder.

The feed roller 114 is driven by an appropriately controlled motor 126 and the feed roller 113 is movably mounted and pressed by springs 127 on to the driven feed roller 114 in order to compress the fiber flocks or fiber material delivered from the separator 110 into a lap which the opener cylinder 115 then opens up into fine flocks.

Also, the cylinder 115 can be hollow and be formed with continuous bores 128, so that by way of an air nozzle 129 at that place of the hollow roller, air can be so blown through bores 128 and the fine fiber flocks detached from the cylinder 115 and blown on to the baffle plate 116.

FIG. 11 shows a variant of the apparatus of FIG. 10 to the extent that the fleece 118 is not conveyed vertically by three roller pairs but is conveyed by a first conveyor belt 130, a second conveyor belt 131 and a squeezing roller pair 132.

Like elements have the same references as in FIG. 10 and will not be further described. FIG. 10 should be consulted for the referencing of the detecting and separating elements.

The fine flocks detached from the cylinder 115 and guided by baffle plate 116 drop on to the convey belt 130 and at the output end thereof are compressed by means of a pressing roller 133 into a thin fiber fleece which is transferred to the second conveyor belt 131. The measuring facility 10, 30, 50, 50.1 or 60 measures the fleece 118 between the first belt 130 and the second belt 131. As previously described, the output signal of this facility goes to the signal processor 18, 38, 58 which also calculates the instant of time at which one of the nozzles 124 blows air through the fleece 118, located between the second belt 131 and the squeezing roller pair 132 disposed thereafter.

Two guide plates 134 are provided to guide the fleece near the nozzles 124 and leave between them an aperture (unreferenced) for the passage of the air from the nozzles 124 so that such air together with the removed portion of fleece can be received by the extraction line 125.

A squeezing roller 135 squeezes the fleece 118 against the second conveyor belt 131 at the delivery end thereof in order to produce a satisfactorily guided fleece for the ejecting of the pieces of unwanted material.

In the variants of FIGS. 10 and 11 it is advantageous to use the preferred methods described above in accordance with FIGS. 5 and 8 since conditions for detection are optimal. The facility for recognition of unwanted material has in this case stationary or movable scanning heads (scanning principle).

The considerations set out with reference to the exemplary embodiments using ultrasonic spatial frequency analysis (e.g., FIGS. 3 and 6) are of course also applicable to a corresponding optical spatial frequency analysis.

It will be appreciated by those of ordinary skill in the art that the present invention can be embodied in other specific forms without departing from the spirit or essential characteristics thereof. The presently disclosed embodiment is therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A method of recognizing unwanted material in a flow of fiber material under measurement in the textile industry, comprising the steps of:
   producing a predetermined acoustic, ultrasonic wave field, using a wave generator connected to a signal generator, which interacts with the flow of fiber material, said step of producing further including a step of outputting from an ultrasonic transmitter and an ultrasonic pulse generator a pulsed ultrasonic signal;
   receiving, by wave transducers, the wave filed which has been altered due to wave scatter by interaction between the material being measured and the wave field, said step of receiving further including a step of detecting a signal reflected from the unwanted material by an ultrasonic receiver; and
   deriving information about the structure of the material being measured from electrical signals generated by the wave transducers, said step of deriving further including a step of analyzing a structure of pattern of the material being measured by means of a correlator on the basis of differences in the pulsed ultrasonic signal and the reflected signal.

2. A method according to claim 1, wherein the wave field is further altered by wave absorption.

3. A method according to claim 1, wherein said step of deriving further includes processing the electrical signals.

4. An apparatus for the recognition of unwanted material in a flow of textile fiber material in a spinning plant, comprising:
- at least one wave generator for producing an acoustic, ultrasonic wave field;
- at least one wave receiver for measuring the flow of material;
- a correlator for processing a time difference and intensity difference between an ultrasonic pulse and a reflected echo pulse; and,
- a wave processor responsive to said correlator for deriving information about the material being measured on the basis of interaction between said flow of material and said wave field.

5. An apparatus according to claim 4, wherein the wave processor is connected to separating means for separating unwanted material from the flow of material being measured.

6. An apparatus according to claim 5, wherein the wave processor is connected to display means.

7. An apparatus according to claim 4, further including a wave-focusing system disposed near the flow of material to be measured.

8. An apparatus according to claim 4, further comprising an ultrasonic focusing means for the wave receiver, such focusing means being disposed immediately beyond the flow of material being measured on a side of said flow of material opposite said wave generator.

9. An apparatus according to claim 8, further comprising an ultrasonic focusing system for the wave generator, said focusing system being disposed immediately before the flow of material being measured on the same side of said flow of material as said wave generator is located.

10. An apparatus according to claim 4, wherein said correlator is connected to a display means of a separator facility.

11. An apparatus according to claim 4, wherein said wave generator and said wave receiver are combined as a transmitting and reflecting measuring facility, and said wave processor further includes a correlator.

12. An apparatus according to claim 4, further including a separator facility connected to said wave processor.

13. An apparatus according to claim 12, further including a display connected to said wave processor.

14. An apparatus according to claim 13, wherein the separator facility is a tube switch in a pneumatic conveying tube receiving the flow of material being measured and is controlled by said wave processor.

15. An apparatus according to claim 13, wherein the separator facility further comprises three squeezing roller pairs disposed consecutively in the direction of conveyance of a fiber fleece clamped between the rollers of such pairs, with the wave generator, wave receiver and wave processor being disposed between the first squeezing roller pair and the second squeezing roller pair and the separator facility being disposed between the second squeezing roller pair and the third squeezing roller pair, the separator facility having a predetermined number of nozzles disposed in a row transversely to a direction of conveyance of the fiber fleece, and an exit orifice of the blowing nozzles being disposed immediately above the fiber fleece, and on a side of the material which is remote from the blowing nozzles, an equal number of suction nozzles are disposed opposite the blowing nozzles, an intensity, an instant of time and a selection of the corresponding blowing nozzle being controlled by the wave processor.

16. An apparatus according to claim 13, wherein a conveyor belt is associated with each of first and second squeezing roller pairs for supplying a fiber fleece to each of the roller pairs, and the wave generator, wave receiver and wave processor are disposed between the first squeezing roller pair and the conveyor belt of the second squeezing roller pair.

17. An apparatus according to claim 13, wherein the separator facility is a junction in a pneumatic conveying tube receiving the flow of material being measured and is controlled by said wave processor.

18. An apparatus for the recognition of unwanted material in a fiber material being prepared for spinning into textile yarn comprising:
- means for outputting radiation as a pulsed, ultrasonic wave field of a wavelength adapted to the dimensions of the unwanted material;
- means for receiving said radiation as a signal reflected from the unwanted material to detect characteristics of said unwanted material which distinguish said unwanted material from said fiber material, said means for receiving further including a correlator for analyzing a structure or pattern of the material being measured on the basis of differences in the pulsed ultrasonic signal and the reflected signal.

19. An apparatus according to claim 18, wherein the fiber material flows in a pneumatic conveying system of a spinning plant blow room.

20. An apparatus according to claim 18, wherein said receiving means reacts to wanted fiber material with a relatively flat image and to unwanted material with a relatively peaky image.

21. Apparatus according to claim 18, wherein said radiation has a wavelength of at least 0.1 millimeters.

22. A method for detecting the presence of unwanted material in cotton being prepared for spinning into textile yarn comprising the steps of:
- introducing a mass of cotton fibers to be examined for presence of unwanted material into an acoustic ultrasonic wave field of pulsed waves having a wavelength at least 0.1 millimeters long;
- sensing waves that have been reflected by at least a portion of said mass of fibers to detect waves reflected from unwanted material; and
- evaluating whether the sensed waves have predetermined characteristics not attributed to the presence of the cotton fibers in the mass, said step of evaluating further including a step of analyzing a structure or pattern of the material being measured by correlating differences in the pulsed ultrasonic wave and the reflected waves.

23. A method according to claim 22, further comprising the step of:
- separating the unwanted material from the mass of fibers.

* * * * *